US00PP20931P2

(12) United States Plant Patent
De Jong

(10) Patent No.: US PP20,931 P2
(45) Date of Patent: Apr. 13, 2010

(54) ***SYMPHORICARPOS* PLANT NAMED 'KOLMCAN'**

(50) Latin Name: *Symphoricarpos alba*
Varietal Denomination: Kolmcan

(75) Inventor: Jan De Jong, Heelsum (NL)

(73) Assignee: Kolster Beheer B.V., Boskoop (NL)

( * ) Notice: Subject to any disclaimer, the term of this patent is extended or adjusted under 35 U.S.C. 154(b) by 0 days.

(21) Appl. No.: 12/315,307

(22) Filed: Dec. 2, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—June Hwu
(74) *Attorney, Agent, or Firm*—C. A. Whealy

(57) ABSTRACT

A new and distinct cultivar of *Symphoricarpos* plant named 'Kolmcan', characterized by its compact, upright and outwardly spreading plant habit; short stems and internodes, bushy and dense habit; freely flowering habit; numerous dark pink-colored berries; and good garden performance.

3 Drawing Sheets

Botanical designation: *Symphoricarpos alba*
Cultivar denomination: 'KOLMCAN'

BACKGROUND OF THE INVENTION

The present invention relates to a new and distinct cultivar of *Symphoricarpos* plant, botanically known as *Symphoricarpos alba* and hereinafter referred to by the name 'Kolmcan'.

The new *Symphoricarpos* plant is a product of a planned breeding program conducted by the Inventor in Heelsum, The Netherlands. The objective of the breeding program is to create new pot-type *Symphoricarpos* cultivars with strong foliage and numerous attractive fruits.

The new *Symphoricarpos* plant originated from a cross-pollination in 2001 in Heelsum, The Netherlands of a proprietary selection of *Symphoricarpos alba* identified as code number 00-06, not patented, as the female, or seed parent with a proprietary selection of *Symphoricarpos alba* identified as code number 99-11, not patented, as the male, or pollen, parent. The new *Symphoricarpos* was discovered and selected by the Inventor as a single flowering plant within the progeny of the stated cross-pollination in a controlled greenhouse environment in Heelsum, The Netherlands in 2003.

Asexual reproduction of the new *Symphoricarpos* plant by vegetative cuttings in Boskoop, The Netherlands since 2003 has shown that the unique features of this new *Symphoricarpos* plant are stable and reproduced true to type in successive generations.

SUMMARY OF THE INVENTION

Plants of the new *Symphoricarpos* have not been observed under all possible environmental conditions. The phenotype may vary somewhat with variations in environment such as temperature and light intensity without, however, any variance in genotype.

The following traits have been repeatedly observed and are determined to be the unique characteristics of 'Kolmcan'. These characteristics in combination distinguish 'Kolmcan' as a new and distinct cultivar of *Symphoricarpos:*

1. Compact, upright and outwardly spreading plant habit.
2. Short stems and internodes, bushy and dense habit.
3. Freely flowering habit.
4. Numerous dark pink-colored berries.
5. Good garden performance.

Plants of the new *Symphoricarpos* differ primarily from plants of the female parent selection in the following characteristics:

1. Plants of the new *Symphoricarpos* have darker green-colored leaves than plants of the female parent selection.
2. Plants of the new *Symphoricarpos* and the female parent selection differ in fruit color as plants of the female parent selection have white-colored berries.

Plants of the new *Symphoricarpos* differ primarily from plants of the male parent selection in the following characteristics:

1. Plants of the new *Symphoricarpos* have shorter lateral branches than plants of the male parent selection.
2. Plants of the new *Symphoricarpos* have lighter pink-colored fruits than plants of the male parent selection.

Plants of the new *Symphoricarpos* can be compared to plants of *Symphoricarpos* 'Scarlet Pearl', disclosed in U.S. Plant Pat. No. 13,244. Plants of the new *Symphoricarpos* differ primarily from plants of 'Scarlet Pearl' in plant habit as plants of the new *Symphoricarpos* are more compact and denser than plants of 'Scarlet Pearl'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Symphoricarpos.* The photograph on the first sheet comprises a side perspective view of a typical plant of 'Kolmcan' grown in a container. The photograph on the second sheet is a close-up view of typical leaves of 'Kolmcan'. The photograph at the top of the third sheet is a close-up view of typical developing and open flowers of 'Kolmcan'; the photograph at the bottom of the third sheet is a close-up view of typical fruits of 'Kolmcan'.

DETAILED BOTANICAL DESCRIPTION

Plants used for the aforementioned photographs and following description were grown for two years under conditions which closely approximate commercial *Symphoricar-*

*pos* production conditions in containers in an outdoor nursery in Boskoop, The Netherlands during the summer. During the production of the plants, day temperatures ranged from 7° C. to 30° C. and night temperatures ranged from 3° C. to 16° C. In the following description, color references are made to The Royal Horticultural Society Colour Chart, 2001 Edition, except where general terms of ordinary dictionary significance are used.

Botanical classification: *Symphoricarpos alba* 'Kolmcan'.

Parentage:

*Female, or seed, parent.*—Proprietary selection of *Symphoricarpos alba* identified as code number 00-06, not patented.

*Male, or pollen, parent.*—Proprietary selection of *Symphoricarpos alba* identified as code number 99-11, not patented.

Propagation:

*Type cutting.*—Vegetative cuttings.

*Time to initiate roots.*—About five weeks at 18° C. to 25° C.

*Time to produce a rooted young plant.*—About eight weeks at 18° C. to 25° C.

*Root description.*—Medium in thickness; fibrous; creamy white in color.

*Rooting habit.*—Moderately freely branching; sparse.

Plant description:

*Form/growth habit.*—Perennial shrub. Compact, upright and outwardly spreading plant habit; broadly inverted triangle; short stems and internodes, bushy and dense habit; moderately vigorous growth habit.

*Branching habit.*—Freely basally branching habit with about 37 lateral branches.

*Plant height.*—About 47.4 cm.

*Plant width (spread).*—About 39.7 cm.

*Lateral branch description.*—Length: About 20.1 cm. Diameter: About 2 mm. Internode length: About 3.1 cm. Strength: Strong. Texture: Smooth, glabrous. Color, developing: Close to 184A to 184B. Color, developed: Close to 199C to 199D.

Foliage description:

*Arrangement.*—Opposite, simple.

*Length.*—About 4 cm.

*Width.*—About 3 cm.

*Shape.*—Elliptic.

*Apex.*—Acute to apiculate.

*Base.*—Attenuate.

*Margin.*—Serrate; undulate.

*Texture, upper and lower surfaces.*—Smooth, glabrous; slightly rugose.

*Venation pattern.*—Pinnate.

*Color.*—Developing leaves, upper surface: Close to 143A to 143B. Developing leaves, lower surface: Close to 143C. Fully expanded leaves, upper surface: Close to 137B; venation, close to 144C. Fully expanded leaves, lower surface: Close to 138B; venation, close to 144C.

*Petioles.*—Length: About 4 mm. Diameter: About 1.2 mm. Texture, upper and lower surfaces: Smooth, glabrous. Color, upper and lower surfaces: Close to 148A.

Flower description:

*Flower arrangement and shape.*—Single campanulate flowers arranged in terminal spikes or solitary in leaf axils; freely flowering habit with about 14 flowers per spike. Flowers face outwardly to drooping.

*Fragrance.*—None detected.

*Natural flowering season.*—From July to September in The Netherlands.

*Flower longevity.*—Flowers last about five days on the plant; flowers not persistent.

*Fruit longevity.*—About one month.

*Flower buds.*—Length: About 6 mm. Diameter: About 3 mm. Shape: Orbicular. Color: Close to 185B to 185D.

*Inflorescence size.*—Height: About 2.5 cm. Diameter: About 1.7 cm.

*Flowers.*—Diameter: About 4 mm. Depth (height): About 6 mm.

*Petals.*—Quantity/arrangement: Five in a single whorl; petals fused towards the base. Length: About 6 mm. Width: About 2 mm. Shape: Broadly elliptic. Apex: Broadly acute. Margin: Entire. Texture, upper surface: Pubescent. Texture, lower surface: Glabrous, smooth. Color: When opening and fully opened, upper surface: Close to 186C; towards the apex, close to 186D. When opening and fully opened, lower surface: Close to 186C.

*Sepals.*—Quantity/arrangement: Five in a single whorl; sepals fused below the apices; calyx, funnelform. Length: About 3 mm. Width: About 1 mm. Apex: Acute. Margin: Entire. Texture, upper and lower surfaces: Glabrous, smooth. Color: When opening and fully opened, upper surface: Close to 143B; at the apex, close to 185B to 185C. When opening and fully opened, lower surface: Close to 143B; at the apex, close to 185A.

*Peduncles.*—Strength: Moderately strong. Length: About 2.1 cm. Diameter: About 1 mm. Texture: Smooth, glabrous. Color: Close to 18A to 18B.

*Pedicels.*—Strength: Moderately strong. Length: About 1 mm. Diameter: About 0.8 mm. Texture: Smooth, glabrous. Color: Close to 144A to 144B.

*Reproductive organs.*—Stamens: Quantity per flower: About five. Filament length: About 2 mm. Filament color: Close to N155A. Anther shape: Narrowly oblong. Anther length: About 1 mm. Anther color: Close to 4D. Pollen amount: Scarce. Pollen color: Close to 4C. Pistils: Quantity per flower: One. Pistil length: About 3.5 mm. Stigma shape: Club-shaped. Stigma color: Close to 144B. Style length: About 3 mm. Style color: Close to 157D. Ovary color: Close to 143B.

*Fruits.*—Length: About 1.3 cm Diameter: About 1.1 cm. Shape: Roughly spherical. Texture: Smooth, glabrous. Color: Between 63B and 64C; underside blushed with 65C to 65D.

*Seeds.*—Length: About 3 mm. Diameter: About 2 mm. Color: Close to 158B.

Disease/pest resistance: Plants of the new *Symphoricarpos* have been noted to be resistant to *Puccinia* rust. Plants of the new *Symphoricarpos* have not been observed to be resistant to pests and other pathogens common to *Symphoricarpos*.

Weather/temperature tolerance: Plants of the new *Symphoricarpos* have been observed to tolerate wind, rain and temperatures ranging from about −25° C. to about 40° C.

It is claimed:

1. A new and distinct *Symphoricarpos* plant named 'Kolmcan' as illustrated and described.

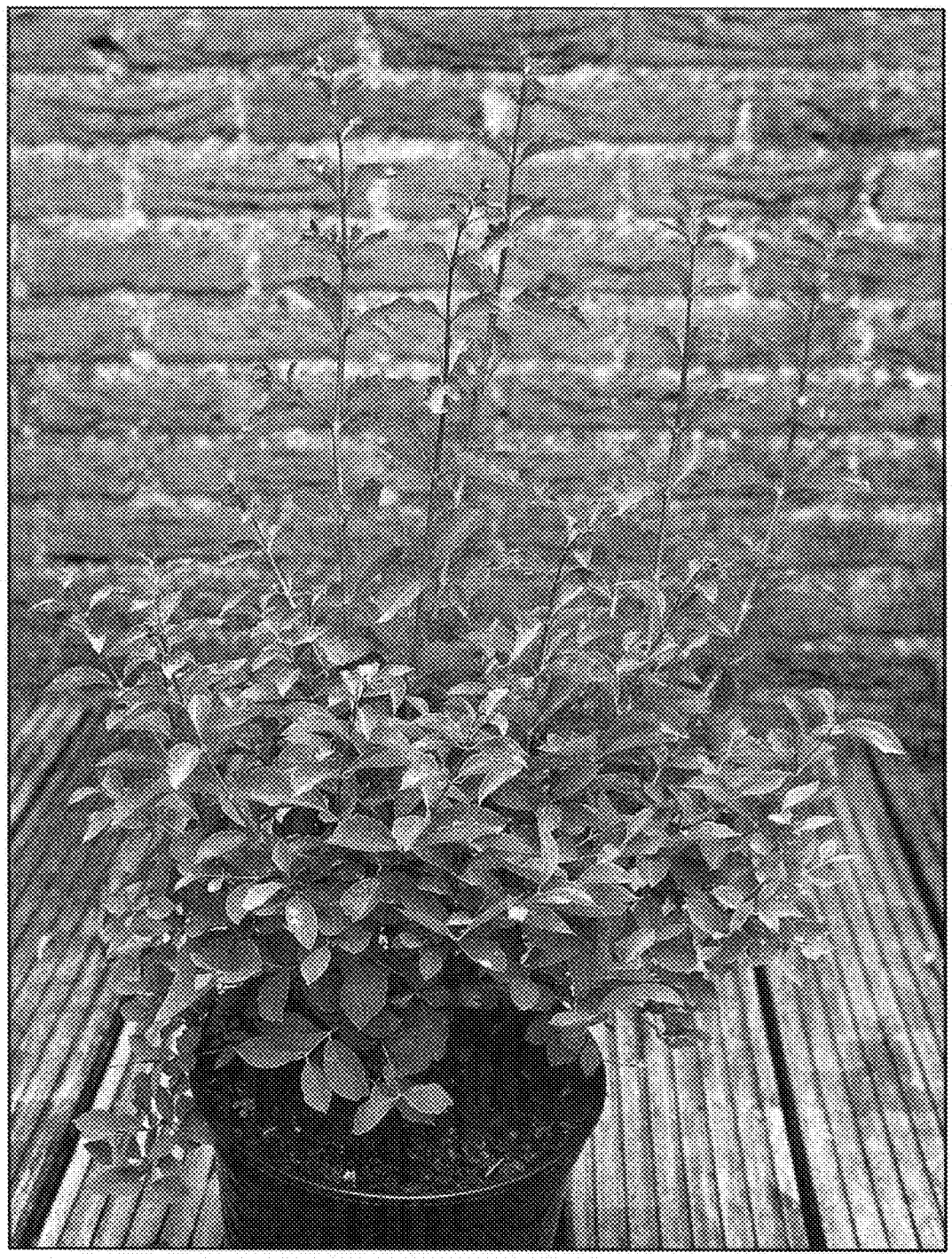

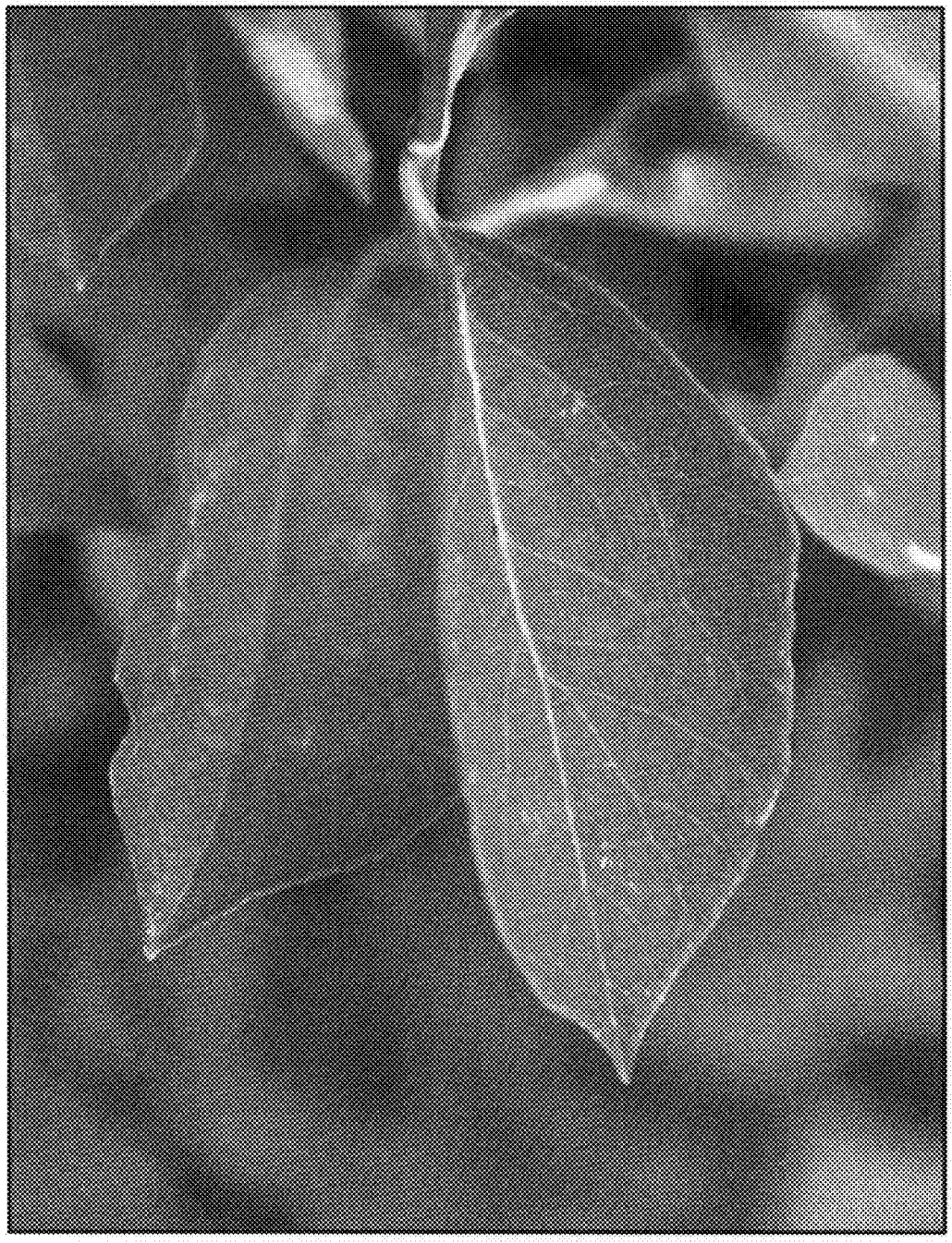

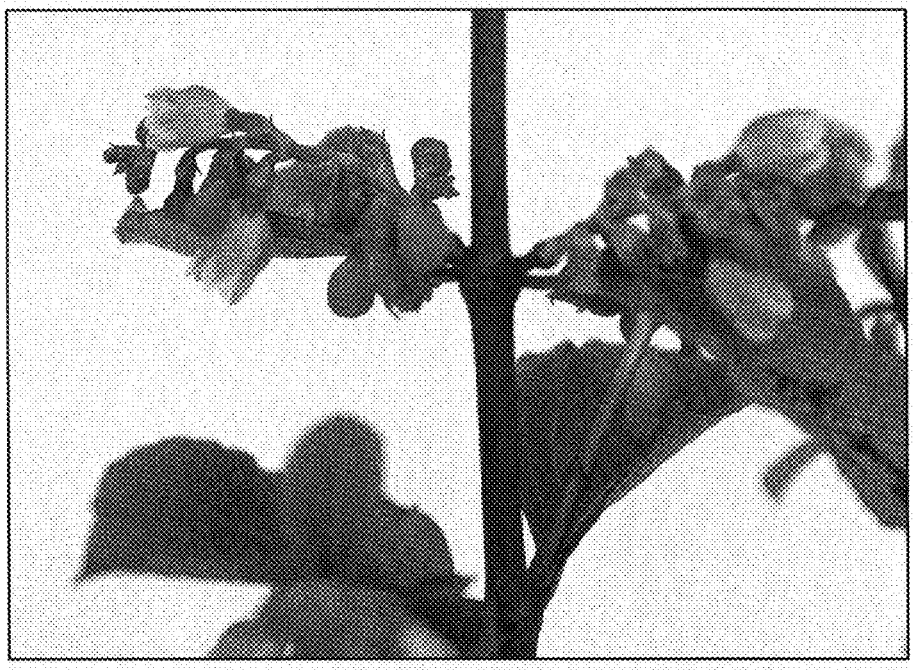
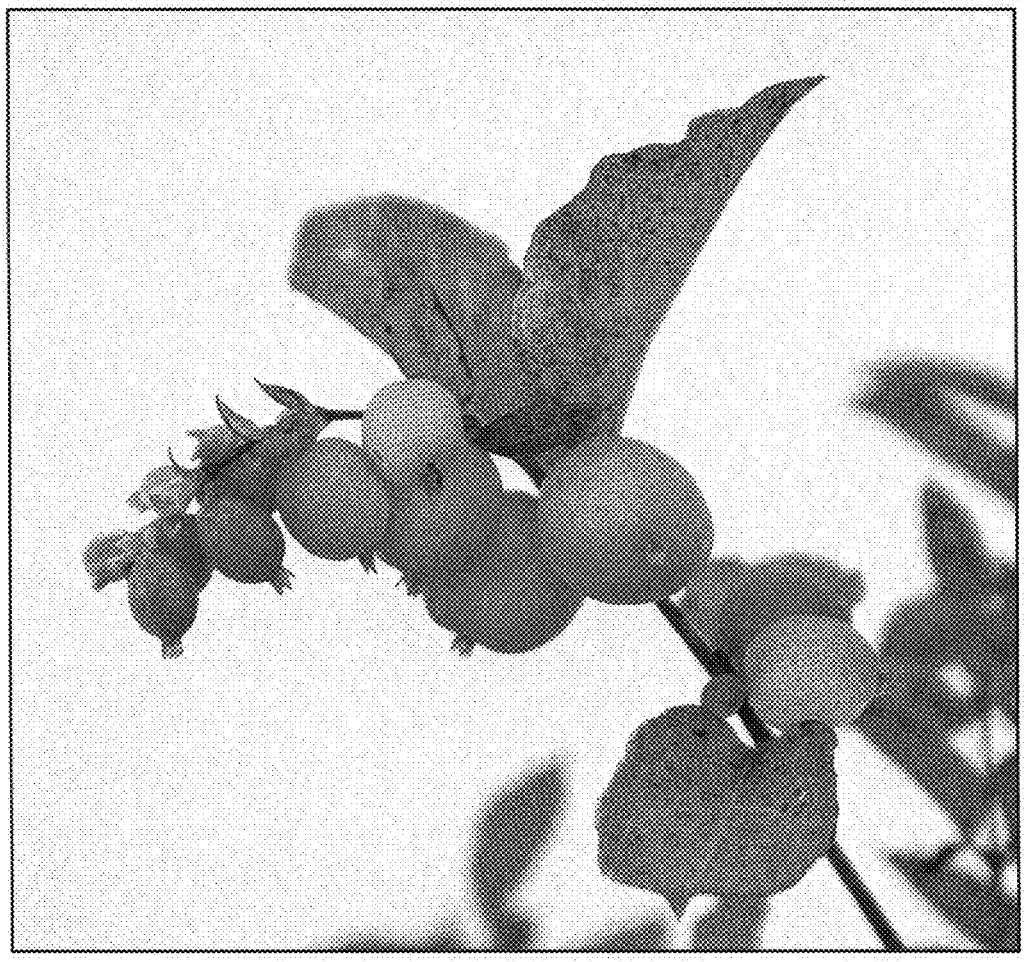

* * * * *